(12) United States Patent
Lurie et al.

(10) Patent No.: US 6,459,933 B1
(45) Date of Patent: Oct. 1, 2002

(54) REMOTE CONTROL ARRHYTHMIA ANALYZER AND DEFIBRILLATOR

(75) Inventors: Keith G. Lurie; Todd M. Zielinski, both of Minneapolis, MN (US)

(73) Assignee: CPRX LLC, Minneapolis, MN (US)

( * ) Notice: Subject to any disclaimer, the term of this patent is extended or adjusted under 35 U.S.C. 154(b) by 0 days.

(21) Appl. No.: 09/564,889

(22) Filed: May 4, 2000

Related U.S. Application Data

(60) Provisional application No. 60/186,008, filed on Mar. 9, 2000.

(51) Int. Cl.⁷ .................................................. A61N 1/39
(52) U.S. Cl. ........................ 607/5; 607/3; 128/204.023; 128/203.014
(58) Field of Search ............................ 607/5, 9, 3, 30, 607/32, 60; 600/16; 128/200.24, 203.14, 204.23

(56) References Cited

U.S. PATENT DOCUMENTS

| 5,551,420 A | | 9/1996 | Lurie et al. | |
| 5,678,535 A | * | 10/1997 | DiMarco | 128/200.24 |
| 5,692,498 A | | 12/1997 | Lurie et al. | 128/205.24 |
| 5,730,122 A | | 3/1998 | Lurie | 128/207.12 |
| 5,975,081 A | * | 11/1999 | Hood et al. | 128/845 |
| 6,029,667 A | | 2/2000 | Lurie | 128/207.16 |
| 6,062,219 A | | 5/2000 | Lurie et al. | 128/205.24 |

FOREIGN PATENT DOCUMENTS

| WO | WO 95/13108 | 5/1995 |
| WO | WO 96/28215 | 8/1996 |
| WO | WO 98/20938 | 5/1998 |
| WO | WO 99/63926 | 12/1999 |
| WO | WO 00/20061 | 4/2000 |

* cited by examiner

Primary Examiner—Jeffrey R. Jastrzab
(74) Attorney, Agent, or Firm—Townsend and Townsend and Crew LLP

(57) ABSTRACT

A method for providing medical treatment to a patient at a location away from a medical facility comprises monitoring at least one physical parameter of a patient that is located away from a medical facility with a monitoring device. The monitored physical parameter is transmitted to a central controller that is located within a medical facility. A control signal is transmitted from the controller to operate a treatment device that is coupled to the patient, with the control signal being selected based at least in part on the monitored physical characteristic.

34 Claims, 3 Drawing Sheets

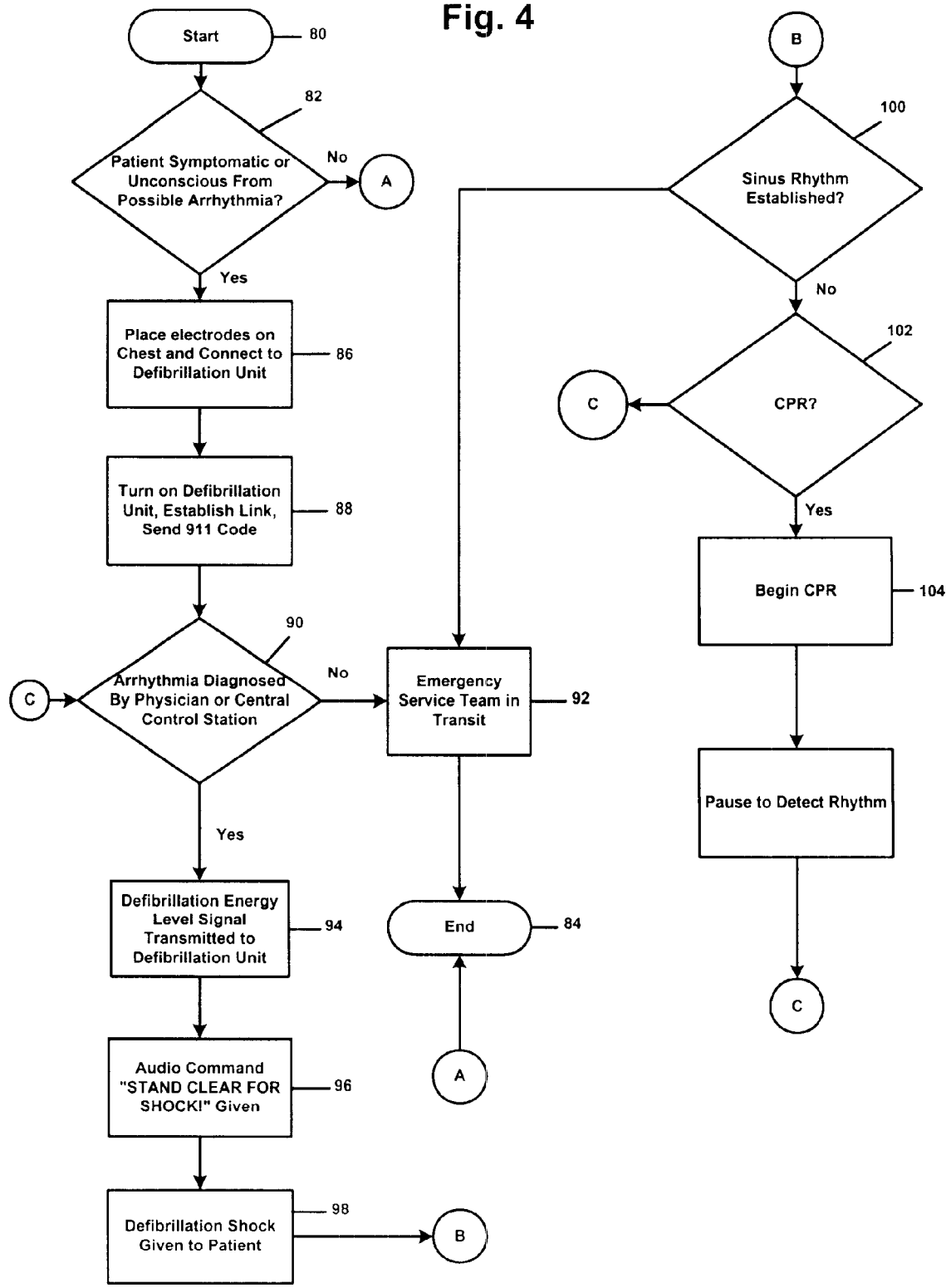

REMOTE CONTROL ARRHYTHMIA ANALYZER AND DEFIBRILLATOR

CROSS-REFERENCES TO RELATED APPLICATIONS

This application is a continuation in part application and claims the benefit of U.S. Provisional Patent Application Serial No. 60/186,008, filed Mar. 1, 2000, the complete disclosure of which is herein incorporated by reference.

BACKGROUND OF THE INVENTION

This invention relates generally to the field of medical treatment, and in particular to the treatment of patients located outside of a medical facility. More specifically, the invention relates to the remote monitoring of patients, and to the remote treatment of such patients based on monitored parameters that have been transmitted to a central control center within a medical facility.

Medical emergencies that occur away from medical facilities are a major concern to medical personnel. The ability to rapidly identify a person's medical condition and to prescribe and administer appropriate remedies is often a critical factor for successful treatment. However, since most medical emergencies occur outside of medical facilities, proper treatment is often limited by the ability to rapidly deploy appropriate medical personnel and equipment. Merely by way of example, for many people, a significant amount of time is spent within their home or at their place of employment. The time required to deploy trained medical personnel and equipment to such locations can play a significant factor in successfully treating individuals experiencing medical emergencies at such venues.

A wide range of medical conditions may pose a significant threat to the health and well being of individuals. Such conditions may include, for example, sudden cardiac arrest, loss of breath, heart attack or heart rhythm abnormality, and the like. As an example, arrhythmias, such as ventricular fibrillation or ventricular tachycardia, are a significant threat of death if not treated promptly and appropriately. One well accepted technique for treating arrhythmias is the application of a defibrillating shock. However, few individuals have the appropriate equipment or training to properly apply a defibrillating shock when the patient is located away from a medical facility. More importantly, even if such equipment were available, trained medical personnel may still be needed to properly diagnose the patient's condition and to prescribe the appropriate treatment.

Hence, the invention is related to techniques for remotely monitoring a patient's condition, diagnosing the patient's condition, as well as remotely applying appropriate treatment schemes. In this way, patients may rapidly be treated outside of a medical facility, while waiting for the arrival of properly trained medical personnel.

SUMMARY OF THE INVENTION

The invention provides systems, devices and methods for remotely monitoring and treating patients suffering from a medical condition or emergency. The invention is particularly useful for patients located outside of a medical facility where immediate access to trained medical personnel is impractical or impossible. According to the invention, the patient is monitored at a remote location where they experience the medical condition. The monitored information is sent over a communication link to a hospital or other medical facility where medical personnel are available to diagnose the condition based on the transmitted information. The monitored information is analyzed by medical personnel and/or by a computer. Control signals may then be transmitted back to a treatment device that is coupled to the patient to medically treat the patient. In this way, the patient may be rapidly diagnosed and treated outside of a medical facility. Once emergency personnel arrive, the patient may be transported to a medical facility for further treatment.

In one particular embodiment, the invention provides a medical monitoring and treatment system that comprises a central controller having at least one communication device for receiving monitoring signals and for transmitting treatment control signals. At least one remote device having at least one communication device for receiving treatment control signals and for transmitting monitoring signals is also provided. The system further includes at least one monitoring device and at least one treatment device that may each be electrically coupled to the remote device. In this way, the remote device may be used to transmit monitoring signals received from the monitoring device to the central controller. The central controller may then be operated to produce and send a treatment control signal back to the remote device to control the treatment device.

The communication devices of the central controller and the remote device may be configured to communicate over a variety of communications links, including, for example, telephone lines, computer networks, including the Internet, cable lines, radio frequency transmission links, satellite transmission links and the like. In this way, the remote device may communicate with trained medical personnel at essentially any location.

The system may include a wide variety of monitoring devices, including, for example, heart monitors, respiratory profile monitors, temperature monitors and the like. Similarly, the system may include a variety of treatment devices, including, for example, positive pressure ventilators, electroventilators, phrenic nerve stimulators, defibrillators, cardiac pacemakers and the like.

In one particular aspect, the treatment device comprises one or more external stimulating electrodes. In this way, the central controller may include a shock control module for sending control signals to the remote device to provide an external defibrillating shock to the patient. The central controller may also include a stimulation control module for sending control signals to the remote device to electrically stimulate the phrenic nerve. Such stimulation may be used to electrically ventilate the patient and/or to assist in lowering the intrathoracic pressure of the patient when performing CPR as described generally in copending U.S. patent application Ser. No. 09/095916 (filed Jun. 11, 1998) and Ser. No. 09/197286 (filed Jan. 20, 1998), the complete disclosures of which are herein incorporated by reference.

In another aspect, the treatment device may comprise a positive pressure ventilator, and the central controller may include a ventilation control module for sending control signals to operate the ventilator. In still another aspect, the treatment device may comprise an external cardiac pacemaker, and the central controller may include a pacemaker control module for sending control signals to operate the pacemaker.

Conveniently, the remote device may include a speaker and circuitry to produce an audible signal or message transmitted from the central controller. In this way, medical personal may remotely provide instructions to a rescuer by speaking into a microphone of the central controller. Further, the speaker may be used to produce warning signals when operating the treatment devices. For example, the speaker may produce an audible warning to "stand back" when a defibrillating shock is about to be applied. Optionally, the remote device may include a camera and circuitry to transmit image signals from the camera to the central controller. Conveniently, the central controller may include a display screen to visually display images produced from the image signals. In this way, medical personnel may remotely visually monitor the patient.

In still another aspect, the central controller may include a monitoring screen to visually display monitoring signals received from the remote device. For example, the monitor may display the patient's heart rhythm in real time.

The invention further provides an exemplary method for providing medical treatment to a remotely located patient. According to the method, at least one physical parameter of a patient that is located away from a medical facility is monitored with a monitoring device. The monitored physical parameter is transmitted in real time to a central controller that is located within a medical facility. A control signal is then sent back from the controller to operate a treatment device that is coupled to the patient, with the control signal being selected based at least in part on the monitored physical characteristic.

Conveniently, the monitored physical parameter may be displayed at the central controller, and then evaluated by medical personnel and/or a computerized analyzer (which may be incorporated into the central controller) so that the central controller may be operated to select and transmit an appropriate control signal. In one aspect, the monitoring device and the treatment device are electrically coupled to a remote device, and the monitored physical parameter is transmitted to the central controller from the remote device. The transmitted control signal may then be sent from the central controller to the remote device to control operation of the treatment device. Conveniently, the monitored physical characteristic and the control signal may be transmitted in real time over a variety of communications links, including, for example, telephone lines, computer networks, cable lines, radio frequency transmission links and satellite transmission links.

In one aspect of the method, the monitored physical characteristic may be any one of a variety of characteristics. Such characteristics may include, for example, arrhythmias, ventricular fibrillation, ventricular tachycardia, end tidal $CO_2$, $O_2$ saturation, inspiratory tidal volume, expiratory tidal volume, patient temperature and the like.

In another aspect, the treatment device may comprise at least one electrode, and the transmitted control signal may be used to control actuation of the electrode to stimulate the phrenic nerve. In this way, the electrode may be used to electroventilate the patient, to increase the negative intrathoracic pressure within the patient and/or to perform electronic CPR on the patient. Further, the transmitted control signal may be used to control actuation of the electrode to supply a delibrillating shock to the patient.

In an alternative aspect, the treatment device may comprise an external pacemaker, and the transmitted control signal may be used to control operation of the pacemaker. Alternatively, the treatment device may comprise a positive pressure ventilator, and the transmitted control signal may be used to control operation of the ventilator.

Conveniently, the remote device may include a speaker, and a signal containing verbal instructions may be transmitted to the remote device to permit the instructions to be recited by the speaker. In another aspect, the remote device may include a camera, and a signal containing visual images may be transmitted from the camera of the remote device to controller for display by the controller.

BRIEF DESCRIPTION OF THE DRAWINGS

FIG. 4 is a flow chart illustrating one method for monitoring and treating an arrhythmia according to the invention.

DESCRIPTION OF THE SPECIFIC EMBODIMENTS

Figure 1:
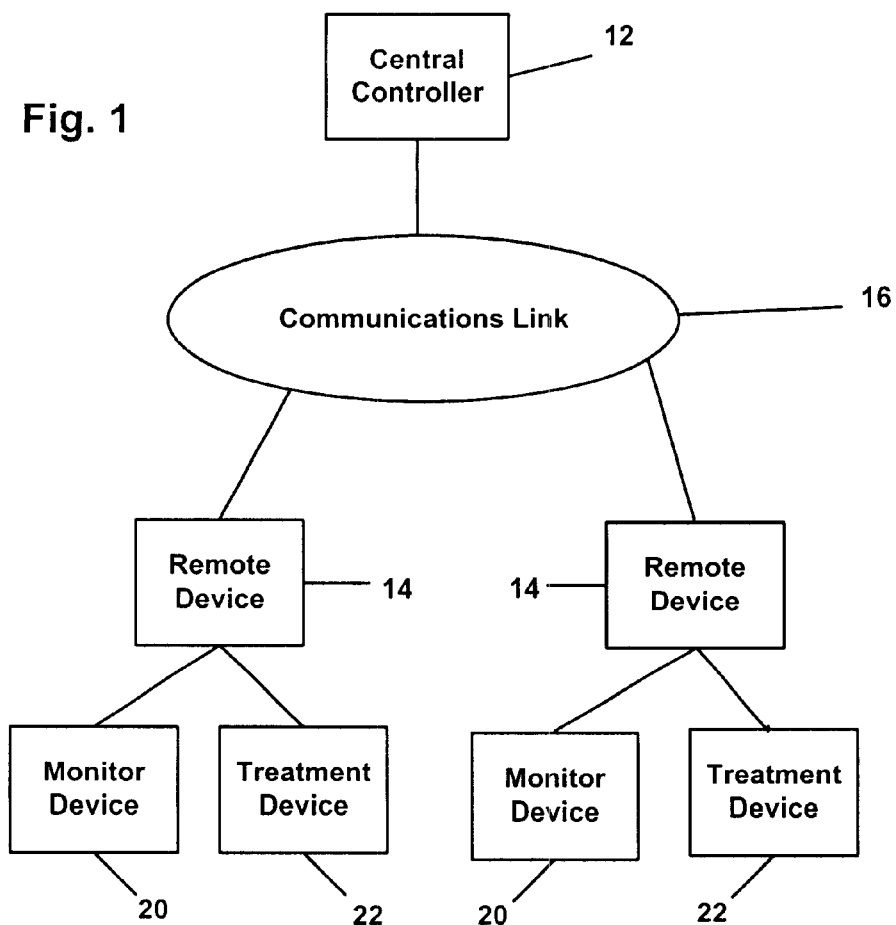
FIG. 1 is a block diagram of a medical monitoring and treatment system according to the invention.

The invention provides equipment and techniques for remotely monitoring and treating a patient located outside of a medical facility. In one aspect, the invention utilizes a communications link between a central control center and a remote patient location outside the hospital to permit real time monitoring and treatment. Conveniently, the system may include a monitoring/control central station that monitors various patient parameters via surface electrodes attached to or implanted within the patient. The central station also has the ability to optionally analyze the monitored signals and to control various remote devices that will aid in shocking ventricular fibrillation and in improving the physiological status or resuscitating/rescuing the subject. This may include, for example, the ability to detect and diagnose arrhythmias and deliver a defibrillating shock to a patient after detecting ventricular fibrillation (VF) or ventricular tachycardia (VT) by the monitoring system.

The system may employ a two-way communication link between the central station and remote patient location to permit real time monitoring and control of any treatment devices. The remote patient location may be located anywhere outside of a medical facility or other building in which the central station resides. For example, the central station may reside in a hospital emergency department in which the on-call physician controls the remote device and/or communicates with the rescuer at the patient site. Alternatively, the central station may include a computerized system capable of receiving and analyzing a remote signal, processing the information and transmitting back treatment information to the device used to treat the patient. As one specific example, the remote site may reside at the patient's home. However, if a portable device is used, the remote unit may operate anywhere the communication link can be established. Two-way communication between each site may be established via dedicated telephone lines or dedicated modem links through a computer, television, specially designed electronic device or the like. Satellite or radio-frequency links may also be used as a communication link.

At the remote patient location, various electronic devices may be controlled by signals generated from the central station and transmitted via a communication link to the remote patient site, thus actuating the electronic device(s) at the applicable time or timing cycle. Audio commands may also be given by the physician (or programmed into the remote device) to the rescuer, thus aiding in the rescue efforts. Additionally, video monitoring may occur by the physician to view the rescue attempt in situ.

Devices that may be used as monitoring equipment at the control and remote sites include, for example: heart monitors, respiratory profile monitors (that monitor end tidal $CO_2$, $O_2$ saturation, inspiratory and expiratory tidal volume, and the like), patient temperature, and the like. Devices that may be used as controllable equipment located at the remote site and controlled either at the remote site or hospital control site include, for example: positive pressure ventilators, electroventilators and/or phrenic nerve stimulators, defibrillators, cardiac pacemakers, and the like.

Upon arrival of additional trained personnel to the remote site, the controllable equipment located at the remote site may be actuated by either the physician at the central control center or the trained personnel located at the remote site. Feedback via monitors or voice communication links to the physician at the hospital control center permit subject status to be continuously monitored throughout the rescue attempt.

The device may be a portable telecommunication link or a more complex system designated to reside solely in the patient's home. The portable device may include an audio/visual two-way communication link that may include an external cardiac pacemaker, an electroventilator and/or phrenic stimulator, and an external defibrillator as controllable devices. Respiratory and heart monitoring components may also be contained in this device. The stationary system residing in the patient's home may contain all the controllable and monitoring equipment previously mentioned.

One non-limiting example is where a patient is observed to collapse. A pair of electrodes is attached to his/her anterior chest and under the left axilla by a rescuer, if not already in place. The electrodes may be attached to a defibrillator for remote interaction and activation. At the push of a button, a telecommunication link is established by the defibrillator unit via a modem link to the central control station. Simultaneously, a 911 "call for help" code may be transmitted to the local emergency rescue station. Cardiac electrograms from the patient may then be transmitted via a modem link to a central control station for diagnosis. A computerized analysis system may also be used at the central control station. Alternatively, a trained medical specialist may make the diagnosis. Once the malignant heart rhythm is confirmed by the physician at the central control station, the defibrillator unit may be activated, an audio alert given, and a shock may be delivered to the patient under control from the central control station. Utilizing this scheme, a rescuer at the scene may simultaneously perform cardiopulmonary resuscitation (CPR). The defibrillator unit may also deliver voice commands, such as "STAND CLEAR FOR SHOCK!" and may also provide feedback via voice commands in the proper performance and cadence of CPR.

This system may be applied to a sick patient or one who has just collapsed with assistance from a rescuer. Utilizing the rapid communication system, information related to the patient's heart rhythm and status may be conveyed to the central control station. The communication input to the central control station may be diagnosed by a computer or trained medical personnel and the appropriate energy defibrillation shock signal may be transmitted back to the remote defibrillation unit. Optionally, a "STAND CLEAR FOR SHOCK!" voice command may also be given, followed by a defibrillation shock delivered to the patient.

As another non-limiting example, a patient arrests at home. The spouse places electrodes on the patient's neck, anteriorly and posteriorly over the cervical 3–6 spine region, and electrodes on the chest over the heart under the left axilla or on the patient's back behind the heart. The patient's head is tilted backwards. The spouse pushes a button on the generator device which connects to the electrodes. This activates a 911 call for help and immediately establishes a communication link with the central control station. The electrodes are connected to a stimulator/defibrillator device. The central command station analyzes the patient's rhythm and directs both the defibrillation energy from the generator device as well as a diaphragmatic stimulation from the stimulation device to cause gasping and/or electrical CPR. Such stimulation techniques are described generally in copending U.S. patent application Ser. No., 09/095916 (filed Jun. 11, 1998) and Ser. No. 09/197286 (filed Jan. 20, 1998), the complete disclosures of which are herein incorporated by reference.

In some cases, a face mask containing an inspiratory impedance valve may also be placed over the patient's mouth and nose for improving CPR efficiency and for assisting in ventilating the patient. This procedure is more fully described in U.S. Pat. Nos. 5,551,420 and 5,692,498, the complete disclosures of which are herein incorporated by reference. If diaphragmatic stimulation is performed automatically, then the spouse can perform chest compressions and ventilate periodically via the face mask. This process and series of devices enable remote control of defibrillation, remote control of phrenic nerve stimulation, and may provide immediate feedback to the lay or professional rescuer(s) until more advanced professional help arrives at the scene.

In another embodiment, other therapy, including drug therapy, may be contained in a locked box. This box may be remotely opened only from a control signal sent from the central control station, and instruction for use may be given remotely. Drug therapy, such as nitroglycerin, adrenalin, aspirin, morphine, oxygen or vasopressin, may be administered by the rescuer at the scene while waiting for a professional responder.

Referring now to FIG. 1, one embodiment of a medical monitoring and treatment system 10 will be described. System 10 includes a central controller 12 having a communications device, such as a modem, network communications card, or the like. In this way, controller 12 may communicate with one or more remote devices 14 that have a similar communications device over a communications link 16. Exemplary communications links include networks, such as the Internet, wireless links, phone lines and the like. Electrically coupled to each remote device 14 is one or more monitoring devices 20 and one or more treatment devices 22. Monitoring devices that may be coupled to remote device 14 include heart monitors, respiratory profile monitors, temperature monitors, and the like. Treatment devices that may be coupled to remote device include positive pressure ventilators, electroventilators, phrenic nerve stimulators, external defibrillators, external cardiac pacemakers and the like.

System 10 is configured so that a patient that is located away from a medical facility may be rapidly treated simply by keeping in close contact with one of the remote devices. If treatment is needed, the patient is coupled to monitoring device 20 and a link is established with central controller 12. Based on the transmitted information, one or more control signals may be sent over link 16 to remote device 14 to operate treatment device 22. For example, one or more electrodes may be coupled to the patient, and an external defibrillating shock may be applied by remote device 14 based on the control signal from central controller 12.

Figure 2:
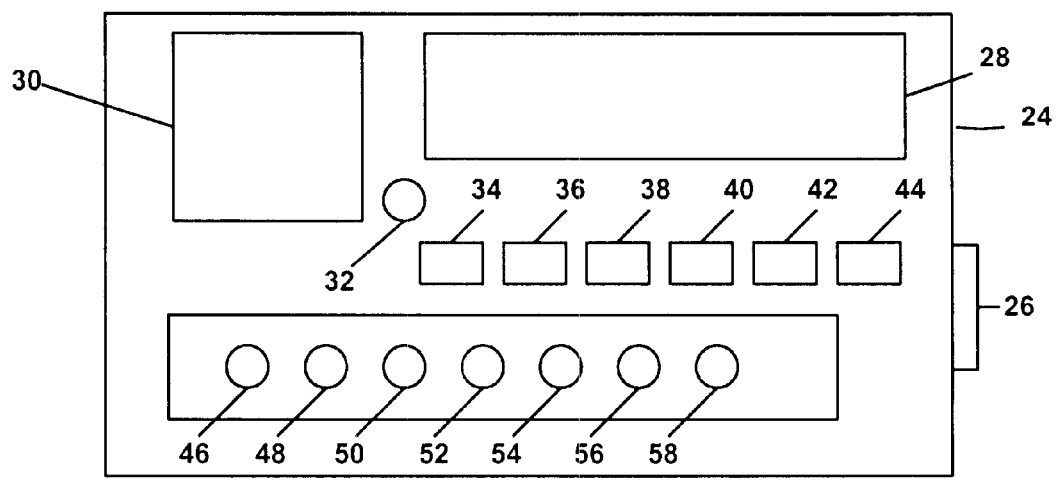
FIG. 2 is a schematic diagram of a central controller of a medical monitoring a treatment system according to the invention.

FIG. 2 illustrates one embodiment of a central controller 24 that may receive monitored signals from a remote device and then send control signals to the remote device. Controller 24 includes a communication device 26 to permit controller 24 to communicate with one or more remote devices over a communications link. Controller 24 further includes a monitoring screen 28 to display in real time any monitored characteristics of the patient as received from the remote device. For example, monitoring screen 28 may display the patient's heart rhythm as measured by an electrode that is coupled to the patient. Monitoring screen 28 may also visually display other characteristics, such as patient temperature, arrhythmias, ventricular fibrillation, ventricular tachycardia, end tidal $CO_2$, $O_2$ saturation, inspiratory tidal volume, expiratory tidal volume, and the like.

Central controller 24 may optionally include a display screen 30 to display real time images captured by the remote device. For example, the remote device may include a video camera and may transmit live video images of the patient. In this way, the medical personnel may visually monitor the treatment at the medical facility. Optionally, a microphone 32 may also be provided to permit the medical personnel to transmit verbal instructions to the remote device over the communications link.

Controller 24 may further include multiple control switches 34–44 to control operation of a particular treatment device that may be coupled to the remote device. For example, switch 34 may comprise a defibrillation control switch that is operated to supply a defibrillating shock to the patient. Switch 36 may comprise a phrenic nerve stimulation switch that is operated to supply a series of electrical pulses to stimulate the phrenic nerve according to a certain pattern. Switch 38 may comprise a ventilator control switch that is operated to actuate a positive pressure ventilator that is coupled to the patient. Switch 40 may comprise a pacemaker control switch used to control operation of a pacemaker that is coupled to the patient.

A variety of adjustment switches 46–58 may also be provided to adjust the control signals sent to the remote device. For example, one of the adjustment switches may be used to control the level of energy ultimately supplied to the electrode when applying a defibrillating shock. As another example, one of the adjustment switches may be used to control the frequency at which a stimulating electrode is actuated. Another adjustment switch may be used to control the rate at which ventilations are supplied. As a further example, another one of the adjustment switches may control the rate of operation of a pacemaker. Further, it will be appreciated that controller 24 may also include an input device to allow controller 24 to be programmed with certain treatment schemes, such as for example, certain phrenic nerve stimulation patterns, certain ventilation schemes, and the like. In this way, medical personnel may simply select a preprogrammed treatment scheme based on the analysis of the monitoring information. In some cases, controller 24 may be programmed to recommend a certain treatment scheme based on the monitoring information. Alternatively, controller 24 may have software to analyze monitored information without actual human interaction. The processed information may be used to generate a remote treatment plan and to send appropriate signals back to the remote device or devices without human interaction.

Figure 3:
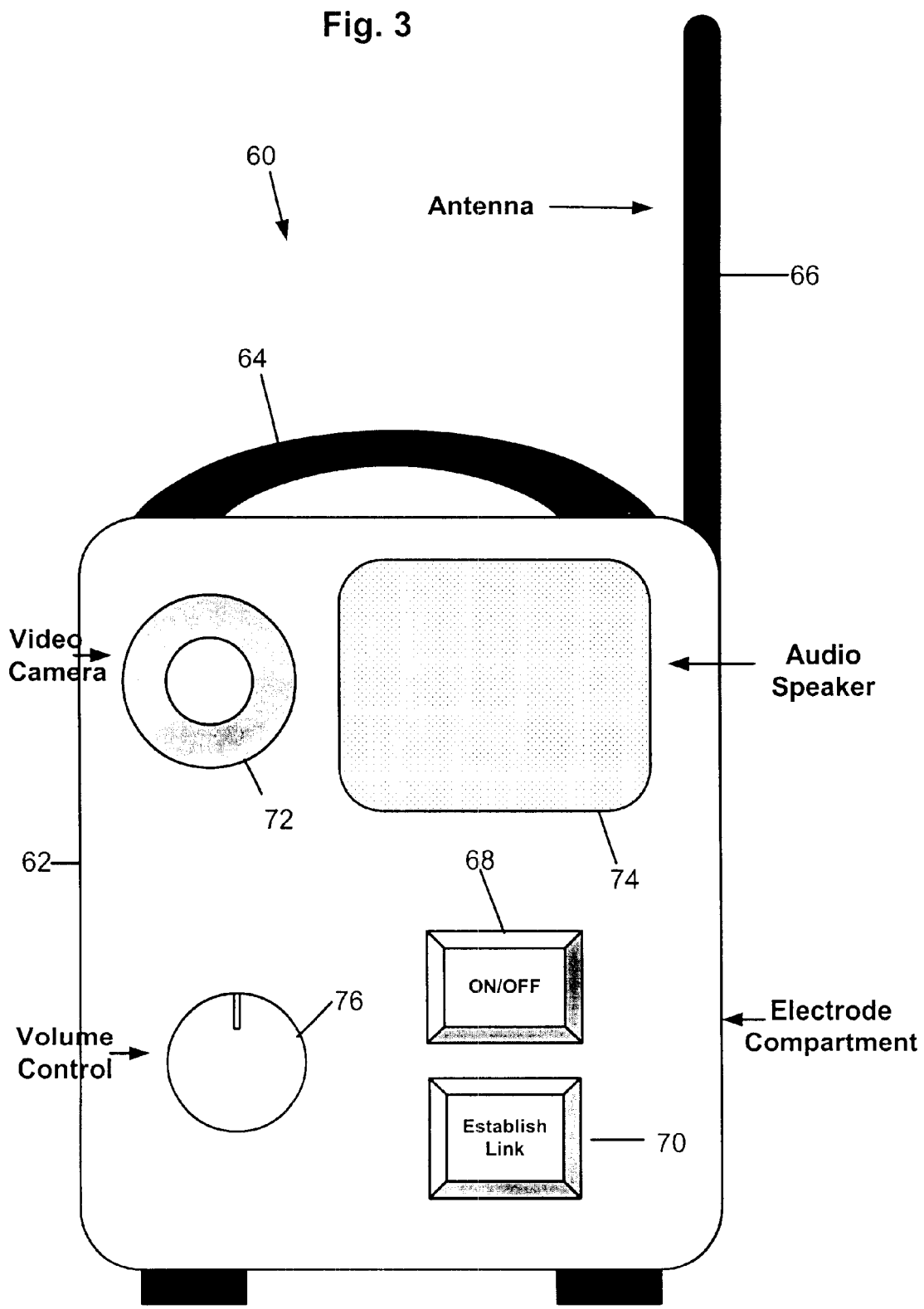
FIG. 3 is a schematic diagram of a remote device of a medical monitoring a treatment system according to the invention.

FIG. 3 illustrates one embodiment of a remote device 60 that may be used with a central controller, such as the controller of FIG. 2, to remotely monitor and treat a patient. Device 60 is constricted of a housing 62 having a handle 64 to facilitate carrying of device 60. Also included is an antenna 66 that permits device 60 to wirelessly communicate with a central controller. Although not shown, device 60 further includes connections to permit one or more monitoring devices and/or treatment devices to be coupled to device 60. An on/off switch 68 is provided to turn device 60 on and off. Further, a link switch 70 is provided to establish a communications link with the central controller when device 60 is turned on and switch 70 is pressed.

A video camera 72 may optionally be provided to permit video images to be transmitted to the central controller. In this way, medical personnel may visually monitor the patient and the applied treatment. Further, an audio speaker 74 may be included to permit verbal instructions to be provided during treatment. For example, a verbal warning may be provided when a defibrillating shock is to be applied. Medical personnel may also give verbal instructions to the central controller that are played in real time using speaker 74. A volume control switch 76 may be used to control the volume level of speaker 74.

Remote device 60 includes appropriate circuitry and power sources to operate any connected monitoring and/or treatment devices. In this way, remote device 60 is capable of transmitting monitoring signals to the central controller as well as to operate the treatment devices based on the control signals sent from the central controller.

Referring now to FIG. 4, one method for treating a patient having an arrhythmia using a central controller and a remote device similar to those described in FIGS. 2 and 3 will be described. The process begins at step 80, and the patient is evaluated by a rescuer to determine if the patient is symptomatic (or unconscious) from possible arrhythmia as shown in step 82. If not, the process ends at step 84. If so, the rescuer places external electrodes on the patient's chest and connects the electrodes to a defibrillation unit of a remote device as shown in step 86. In step 88, the defibrillation unit is turned on and a link is established with the central controller. Optionally, a 911 call may also be placed to an appropriate call center so that medical personnel may be dispatched to the patient's location.

At the central control station, a computerized analyzer and/or trained medical personnel evaluates the information transmitted from the defibrillation unit to determine if an arrhythmia exists as shown in step 90. If not, an emergency team may still be dispatched as shown in step 92 to further evaluate the patient. If an arrhythmia is diagnosed, the process proceeds to step 94 where a defibrillation energy level signal is transmitted to the defibrillation unit to indicate the appropriate energy level of the defibrillating shock. An audio command to "stand clear for shock" may also be given as shown in step 96. In step 98, the defibrillation unit supplies the defibrillation shock to the patient at the appropriate energy level.

The defibrillation unit then monitors the patient and transmits information to the central controller to determine if a stable heart rhythm has been established as shown in step 100. If so, the process proceeds to step 92 where the dispatched emergency team may further evaluate the patient. If not, the process may proceed to step 102 where the medical personnel determine whether CPR should be performed or whether another shock should be applied. If CPR is appropriate, CPR is performed as shown in step 104. Optionally, electronic CPR may be performed based on control signals received from the central controller. Periodically, the rescuer pauses in step 106 to detect a heart rhythm. The process then proceeds back to step 90 where an additional shock may be applied.

The invention has now been described in detail for purposes of clarity of understanding. However, it will be appreciated that certain changes and modifications may be practiced within the scope of the appended claims.

What is claimed is:

1. A medical monitoring and treatment system, comprising:
   a central controller having at least one communication device for receiving monitoring signals and for transmitting treatment control signals;
   at least one remote device having at least one communication device for receiving treatment control signals and for transmitting monitoring signals, wherein the communication device of the remote device includes a switch that is operable to establish a connection with the central controller;
   at least one monitoring device that is adapted to be electrically coupled to the remote device;
   at least one treatment device that is adapted to be electrically coupled to the remote device; and
   a valve that may be interfaced with a patient's airway to regulate intrathoracic pressures within the patient;
   wherein the remote device is configured to transmit monitoring signals received from the monitoring device to the central controller, and to control the treatment device based on control signals received from the central controller.

2. A system as in claim 1, wherein the communication devices of the central controller and the remote device are configured to communicate over a communications link that is selected from a group of links consisting of telephone lines, computer networks, cable lines, radio frequency transmission links and satellite transmission links.

3. A system as in claim 2, wherein the monitoring device is selected from a group of devices consisting of heart monitors, respiratory profile monitors, and temperature monitors.

4. A system as in claim 1, wherein the treatment device is selected from a group consisting of positive pressure ventilators, electroventilators, phrenic nerve stimulators, diaphragm stimulators, external defibrillators, and external cardiac pacemakers.

5. A system as in claim 1, wherein the treatment device comprises at least one electrode that is configured to produce an electrical stimulant or shock to the patient.

6. A system as in claim 1, wherein the remote device further includes a speaker and circuitry to produce an audible signal or message transmitted from the central controller.

7. A system as in claim 1, wherein the remote device further includes a camera and circuitry to transmit image signals from the camera to the central controller, and wherein the central controller further includes a display screen for visually displaying images produced from the image signals.

8. A system as in claim 1, wherein the treatment device comprises at least one pair of external electrodes, and wherein the central controller includes a shock control module that is operable to send a control signal to the remote device to permit the remote device to produce a defibrillating shock using the electrodes.

9. A system as in claim 1, wherein the treatment device comprises at least one pair of external electrodes, and wherein the central controller includes a stimulation control module that is operable to send control signals to the remote device to permit the remote device to produce an electrical stimulant with the electrodes to stimulate the phrenic nerve.

10. A system as in claim 1, wherein the treatment device includes an active electrode that is attachable to the patient to produce a stimulating shock, cardiac pacing or phrenic nerve stimulation.

11. A system as in claim 1, wherein the treatment device comprises a positive pressure ventilator, and wherein the central controller includes a ventilation control module that is operable to send control signals to the remote device to permit the remote device to control the positive pressure ventilator.

12. A system as in claim 1, wherein the treatment device comprises an external cardiac pacemaker, and wherein the central controller includes a pacemaker control module that is operable to send control signals to the remote device to permit the remote device to control operation of the pacemaker.

13. A system as in claim 1, wherein the central controller includes a microphone to receive verbal instructions from medical personnel, and wherein the central controller is configured to transmit an audio signal containing the verbal instructions to the remote device.

14. A system as in claim 1, wherein the central controller further includes a monitoring screen to visually display monitoring signals received from the remote device.

15. A method for providing medical treatment to a patient at a location away from a medical facility, the method comprising:
   monitoring at least one physiological parameter of a patient that is located away from a medical facility with a monitoring device;
   transmitting the monitored physiological parameter to a central controller that is located within a medical facility;
   transmitting a control signal from the controller to operate a treatment device that is coupled to the patient, wherein the control signal is selected based at least in part on the monitored physiological parameter;
   wherein the treatment device comprises at least one pair of electrodes, and wherein the transmitted control signal is used to control actuation of the electrodes to externally stimulate the phrenic nerve and thereby electroventilate the patient, to increase the negative intrathoracic pressure within the patient and/or to perform electronic CPR on the patient; and
   coupling a valve to the patient's airway to regulate gas flow into the patient's lungs during decompression of the patient's chest.

16. A method as in claim 15, further comprising displaying the monitored physiological parameter at the central controller, evaluating the parameter and operating the central controller to select and transmit the control signal.

17. A method as in claim 15, wherein the monitoring device and the treatment device are electrically coupled to a remote device, and further comprising transmitting the monitored physiological parameter to the central controller from the remote device, and receiving the transmitted control signal from the central controller with the remote device.

18. A method as in claim 15, further comprising transmitting the monitored physiological parameter and the control signal over a communications link that is selected from a group consisting of telephone lines, computer networks, cable lines, radio frequency transmission links and satellite transmission links.

19. A method as in claim 15, wherein the monitored physiological parameter is selected from a of group of characteristics consisting of cardiac rhythms, end tidal $CO_2$, $O_2$ saturation, inspiratory tidal volume, expiratory tidal volume, and patient temperature.

20. A method as in claim 15, wherein the transmitted control signal is used to control actuation of at least one of the electrodes to supply an external defibrillating shock to the patient.

21. A method as in claim 15, wherein the treatment device comprises an external pacemaker, and wherein the transmitted control signal is used to control operation of the pacemaker.

22. A method as in claim 15, wherein the treatment device comprises a positive pressure ventilator, and wherein the transmitted control signal is used to control operation of the ventilator.

23. A method as in claim 17, wherein the remote device includes a speaker, and further comprising transmitting a signal containing verbal instructions to the remote device to permit the instructions to be audibilized by the speaker.

24. A method as in claim 17, wherein the remote device includes a camera, and further comprising transmitting a signal containing visual images from the camera of the remote device to controller for display by the controller.

25. A medical control device for controlling operation of a remote treatment device, the control device comprising:
   a processor;
   a communication device that is adapted to receive signals from a remote device containing information on a measured physiological parameter of a patient; and
   at least one control module operable with the processor to produce and send a treatment control signal to the remote device using the communication device to control operation of the remote device;
   wherein the control module comprises a stimulation control module that is operable to send control signals to the remote device to permit the remote device to produce an electrical stimulant with an electrode to stimulate the phrenic nerve when a valve is coupled to the patient's airway to decrease the patient's intrathoracic pressure.

26. A device as in claim 25, wherein the control module comprises a shock control module that is operable to send a control signal to the remote device to permit the remote device to produce a defibrillating shock using an external electrode pair.

27. A device as in claim 25, wherein the remote device is electrically active when in contact with the patient.

28. A device as in claim 25, wherein the control module comprises a ventilation control module that is operable to send control signals to the remote device to permit the remote device to control a positive pressure ventilator.

29. A device as in claim 25, wherein control module comprises an external pacemaker control module that is operable to send control signals to the remote device to permit the remote device to control operation of a pacemaker.

30. A device as in claim 25, further comprising a microphone to receive verbal instructions from medical personnel, and wherein the processor is configured to produce and transmit an audio signal containing the verbal instructions to the remote device.

31. A device as in claim 25, further comprising a monitoring screen to visually display monitoring signals received from the remote device.

32. A portable monitoring and treatment system, comprising:
   a base unit having a processor and a communication device, wherein the communication device comprises a switch that is operable to establish a connection with a central controller;
   a monitoring device connectable to the base unit, wherein the monitoring device is adapted to monitor a physiological parameter of a patient, and wherein the communication device is configured to transmit the monitored parameter to the central controller; and
   a treatment device connectable to the base unit, wherein the treatment device is configured to supply a medical treatment to the patient based on a control signal received from the central controller using the communication device; and
   a valve that may be interfaced with the patient's airway to regulate intrathoracic pressures within the patient.

33. A system as in claim 32, wherein the monitoring device is selected from a group of devices consisting of heart monitors, respiratory profile monitors, and temperature monitors.

34. A system as in claim 32, wherein the treatment device is selected from a group consisting of positive pressure ventilators, electroventilators, phrenic nerve stimulators, defibrillators, and cardiac pacemakers.

* * * * *